(12) United States Patent  
Han et al.

(10) Patent No.: US 7,881,766 B2  
(45) Date of Patent: Feb. 1, 2011

(54) APPARATUS AND METHOD FOR ATTACHING BIOSIGNAL MEASUREMENT SENSOR TO SUBJECT

(75) Inventors: Wan-taek Han, Hwaseong-si (KR); Hyung-sok Yeo, Yongin-si (KR); Kun-soo Shin, Seongnam-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 1141 days.

(21) Appl. No.: 11/434,190

(22) Filed: May 16, 2006

(65) Prior Publication Data

US 2006/0282007 A1   Dec. 14, 2006

(30) Foreign Application Priority Data

Jun. 2, 2005   (KR) .................... 10-2005-0047193

(51) Int. Cl.  
*A61B 5/04* (2006.01)

(52) U.S. Cl. .................. 600/393; 600/396; 600/509

(58) Field of Classification Search ................ 600/509, 600/382, 383, 384, 385, 386, 387, 388, 389, 600/390, 391, 544, 546  
See application file for complete search history.

(56) References Cited

U.S. PATENT DOCUMENTS

| 4,375,219 | A  | * | 3/1983 | Schmid ..................... 600/393 |
| 5,046,504 | A  | * | 9/1991 | Albert et al. ................ 600/509 |
| 6,282,439 | B1 | * | 8/2001 | Ruha ......................... 600/509 |

* cited by examiner

*Primary Examiner*—Carl H. Layno  
*Assistant Examiner*—Jon-Eric C. Morales  
(74) *Attorney, Agent, or Firm*—Sughrue Mion, PLLC

(57) ABSTRACT

An apparatus for attaching a biosignal measurement sensor to a subject including a housing having an open space at one side, an installation portion installed in the open space, on which the biosignal measurement sensor is installed, a plurality of detection electrodes installed at an open side of the housing to contact the subject, and arranged along a circumferential edge of the installation portion to form pairs of detection electrodes facing each other with respect to a center of arrangement, an actuator installed in the housing to rotate and linearly move the installation portion, and a circuit portion searching for the detection electrodes that provide optimal detection data based on a difference in signals between the pairs of detection electrodes, and driving the actuator to allow a pair of sensor electrodes provided at the biosignal measurement sensor to be arranged in the same direction as the searched detection electrodes.

26 Claims, 13 Drawing Sheets

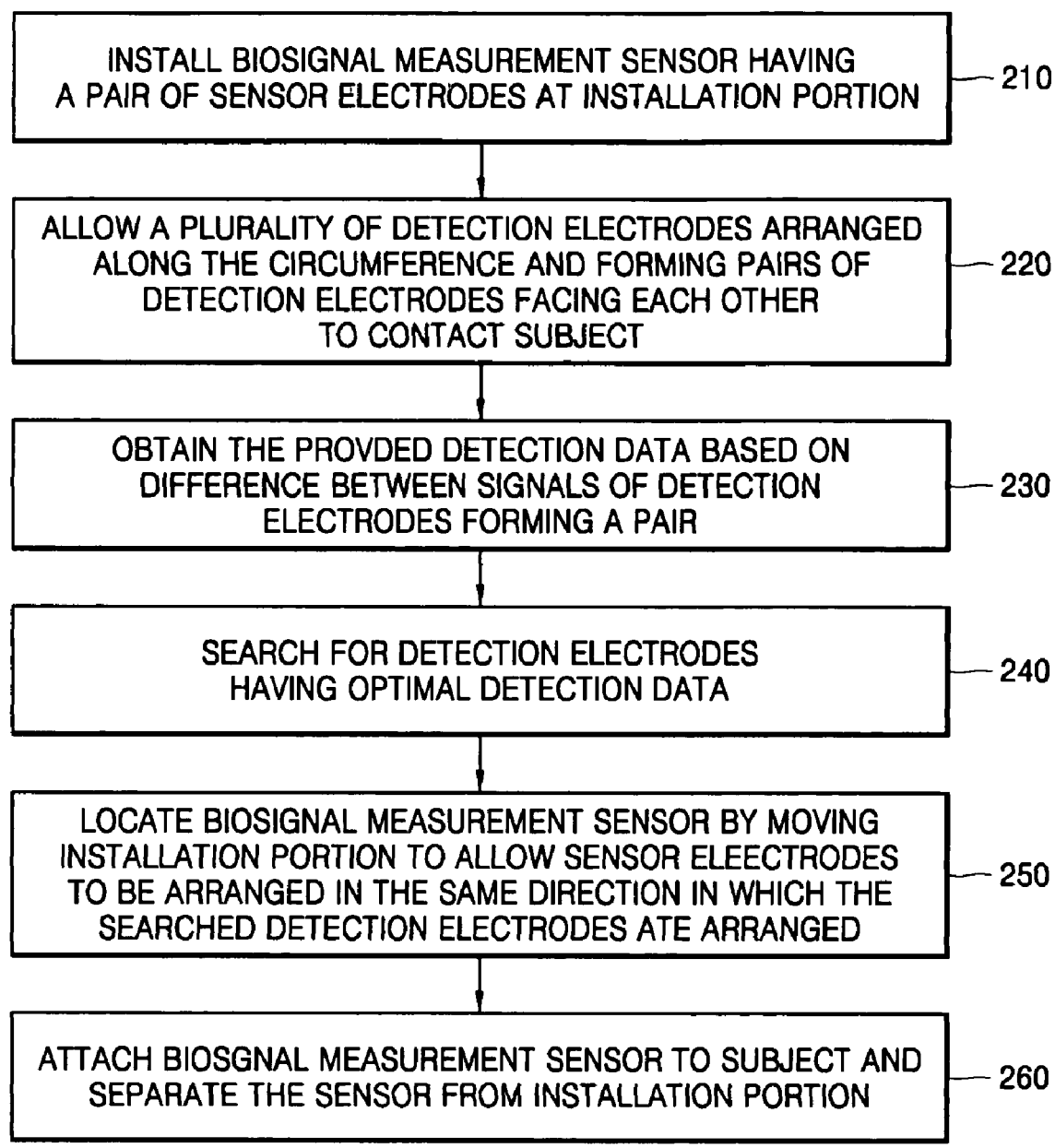

APPARATUS AND METHOD FOR ATTACHING BIOSIGNAL MEASUREMENT SENSOR TO SUBJECT

CROSS-REFERENCE TO RELATED PATENT APPLICATIONS

This application claims priority from Korean Patent Application No. 10-2005-0047193, filed on Jun. 2, 2005, in the Korean Intellectual Property Office, the disclosure of which is incorporated herein in its entirety by reference.

BACKGROUND OF THE INVENTION

1. Field of the Invention

The present invention relates to an apparatus and method for attaching, to a subject, a biosignal measurement sensor that is used to measure a voltage signal generated from a living body.

2. Description of the Related Art

Sensors attached to a living body to collect information generated from the living body include an electrocardiogram (ECG) sensor and an electromyogram (EMG) sensor. The ECG sensor is attached to the chest of a living body to measure a voltage signal generated from the heart. That is, as the heart palpitates, current is generated from the chest and flows along the skin. The ECG sensor is used to measure a voltage difference between two positions on the skin where the current flows using electrodes located at the two positions.

In general, an electrocardiogram is measured by attaching electrodes on the surface of the skin in a method such as a standard limb lead method, a unipolar limb lead method, and a precordial lead method. When the electrodes are not accurately attached to the surface of the skin, a signal having a modified pattern may be generated so that an accurate diagnosis is not available. In other words, the pattern spreading from the heart has different strengths and direction according to the position from the heart. When the electrodes are not appropriately arranged according to the characteristic of the pattern, an accurate signal cannot be obtained. In particular, in the conventional technology, the electrodes are separately and manually attached to the skin. Therefore, a lot of time and expertise are required to accurately arranged and attach all electrodes. If the electrodes are not arranged accurately, incorrect data may be obtained.

To address the above problem, there is an example of forming the electrodes in an integrate body. In this case, however, an accurate diagnosis is difficult because the electrodes are arranged at almost the same positions in spite of the different position of the heart for each patient.

SUMMARY OF THE INVENTION

To address the above and/or other problems, the non-limiting embodiments of the present invention provide an apparatus and method for attaching a biosignal measurement sensor to a subject which allows the biosignal measurement sensor to be accurately and easily attached to any positions of the subject, so that an accurate biosignal is obtained.

According to an aspect of the present invention, an apparatus for attaching a biosignal measurement sensor to a subject comprises a housing having an open space at one side, an installation portion installed in the open space, on which the biosignal measurement sensor is installed, a plurality of detection electrodes installed at an open side of the housing to contact the subject, and arranged along a circumferential edge of the installation portion to form pairs of two detection electrodes facing each other with respect to a center of arrangement, an actuator installed in the housing and rotating and linearly moving the installation portion, and a circuit portion searching for the detection electrodes that provide optimal detection data based on a difference in signals between the detection electrodes forming a pair, and driving the actuator to allow a pair of sensor electrodes provided at the biosignal measurement sensor to be arranged in the same direction in which the searched detection electrodes are arranged.

The optimal detection data is detection data having the maximum correlation coefficient with respect to reference data. The circuit portion comprises a microcontroller which searches the detection electrodes having the detection data having the maximum correlation coefficient by calculating correlation coefficients between the detection data and the reference data, and providing a control signal to the actuator to allow the sensor electrodes to be arranged in the same direction in which the searched detection electrodes are arranged.

The optimal data is the detection data having the maximum peak. The circuit portion comprises a microcontroller which searches the detection electrodes having the detection data having the maximum correlation coefficient by calculating correlation coefficients between the detection data and the reference data, and providing a control signal to the actuator to allow the sensor electrodes to be arranged in the same direction in which the searched detection electrodes are arranged.

According to another aspect of the present invention, a method of attaching a biosignal measurement sensor comprises installing the biosignal measurement sensor having a pair of sensor electrodes at an installation portion, allowing detection electrodes arranged along a circumference to form pairs of the detection electrodes facing to each other, to contact a subject, obtaining detection data from a difference between signals of the detection electrodes forming each of the detection electrode pairs, searching detection electrodes having optimal detection data among the detection data, locating the biosignal measurement sensor by moving the installation portion such that the sensor electrodes are arranged in the same direction in which the searched detection electrodes are arranged, and attaching the biosignal measurement sensor to the subject and then separating the biosignal measurement sensor from the installation portion.

BRIEF DESCRIPTION OF THE DRAWINGS

The above and other features and aspects of the present invention will become more apparent by describing in detail non-limiting embodiments thereof with reference to the attached drawings in which:

FIG. 9 is a flow chart for explaining a method of attaching a biosignal measurement sensor to a subject according to a non-limiting embodiment of the present invention.

DETAILED DESCRIPTION OF THE INVENTION

Figure 1A:
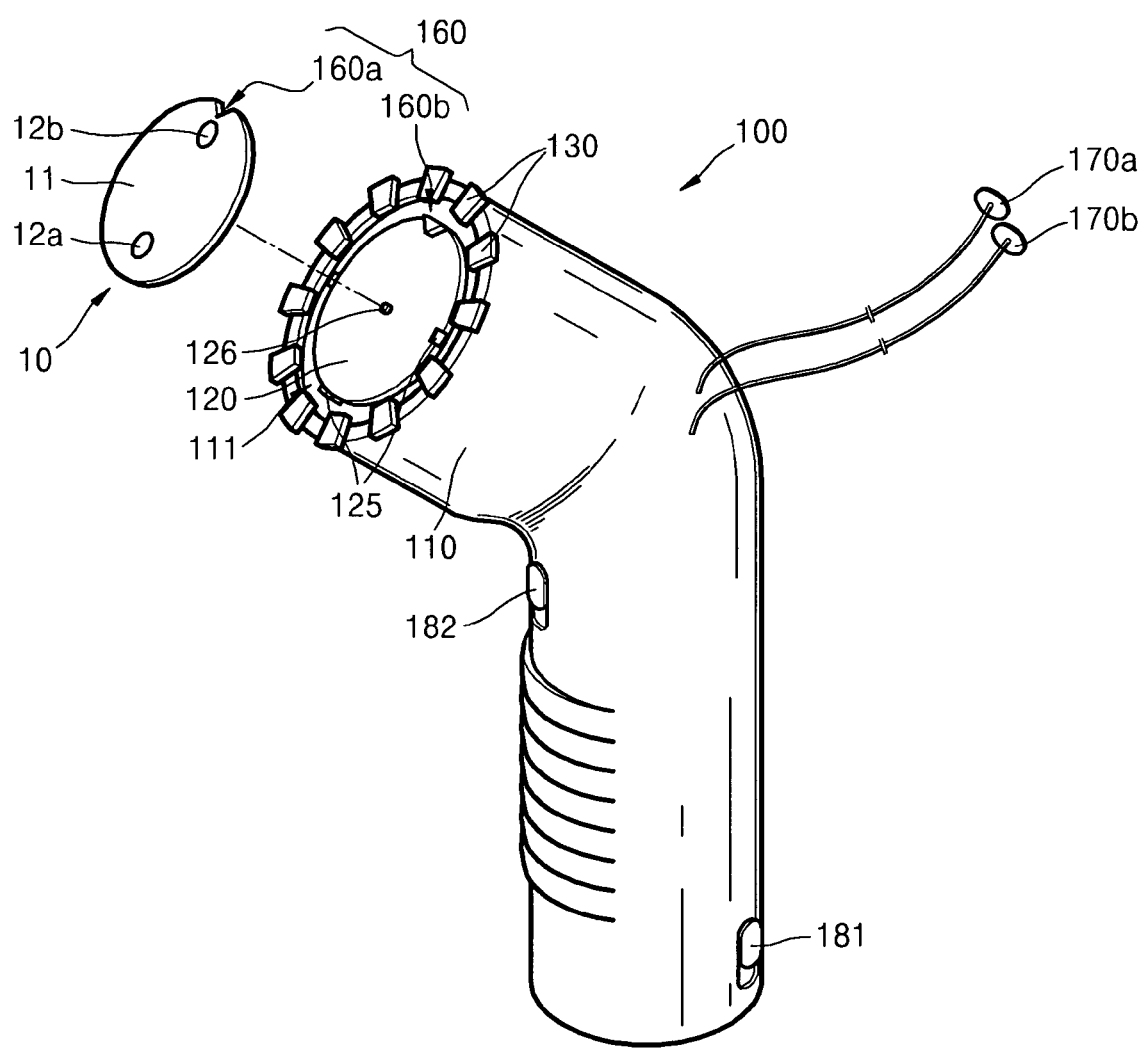
FIG. 1A is a perspective view of an apparatus for attaching a biosignal measurement sensor to a subject according to a non-limiting embodiment of the present invention.
Figure 1B:
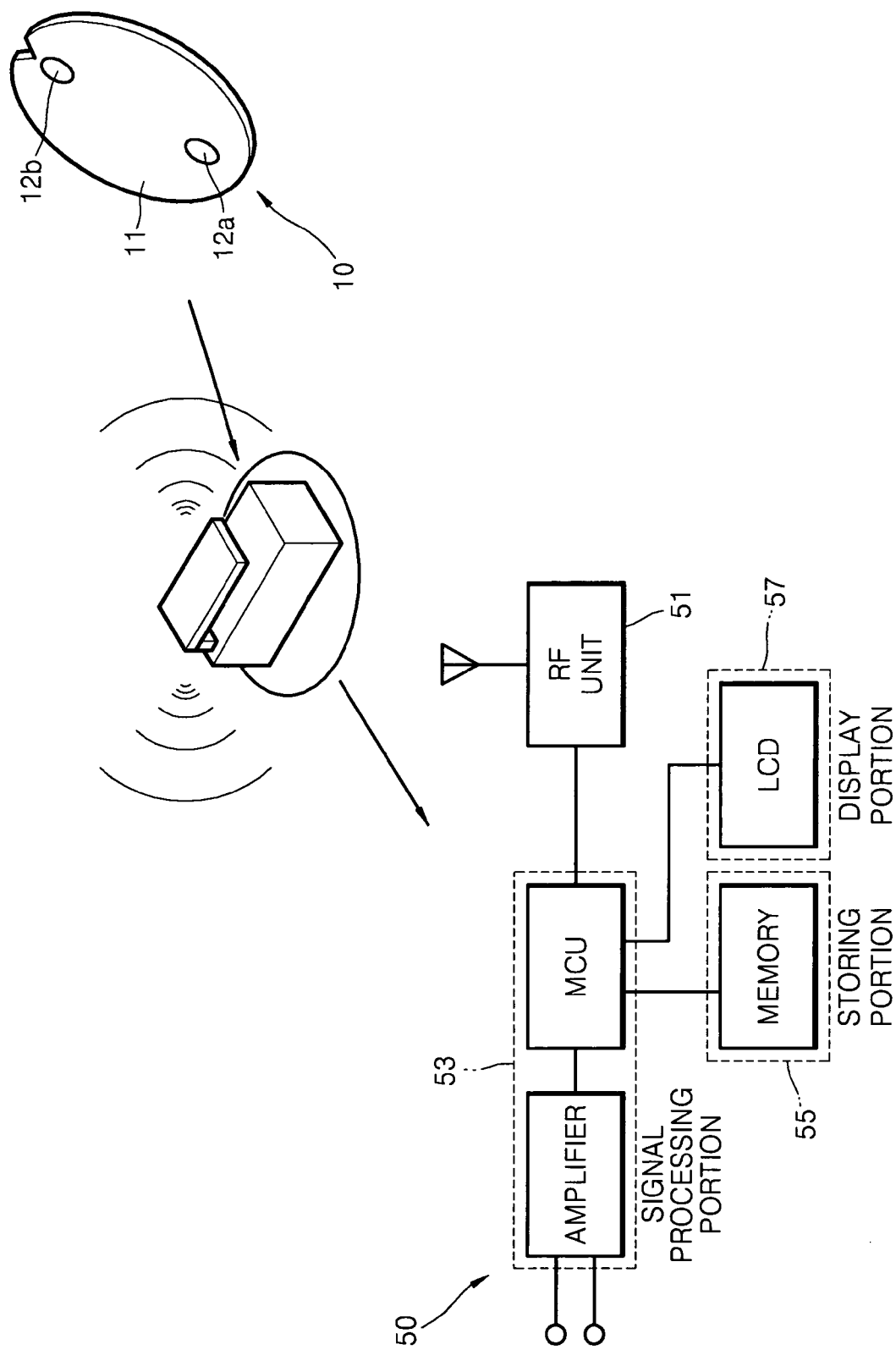
FIG. 1B is a block diagram showing the structure of a receiver to wireless communication with the biosignal measurement sensor.
Figure 2A:
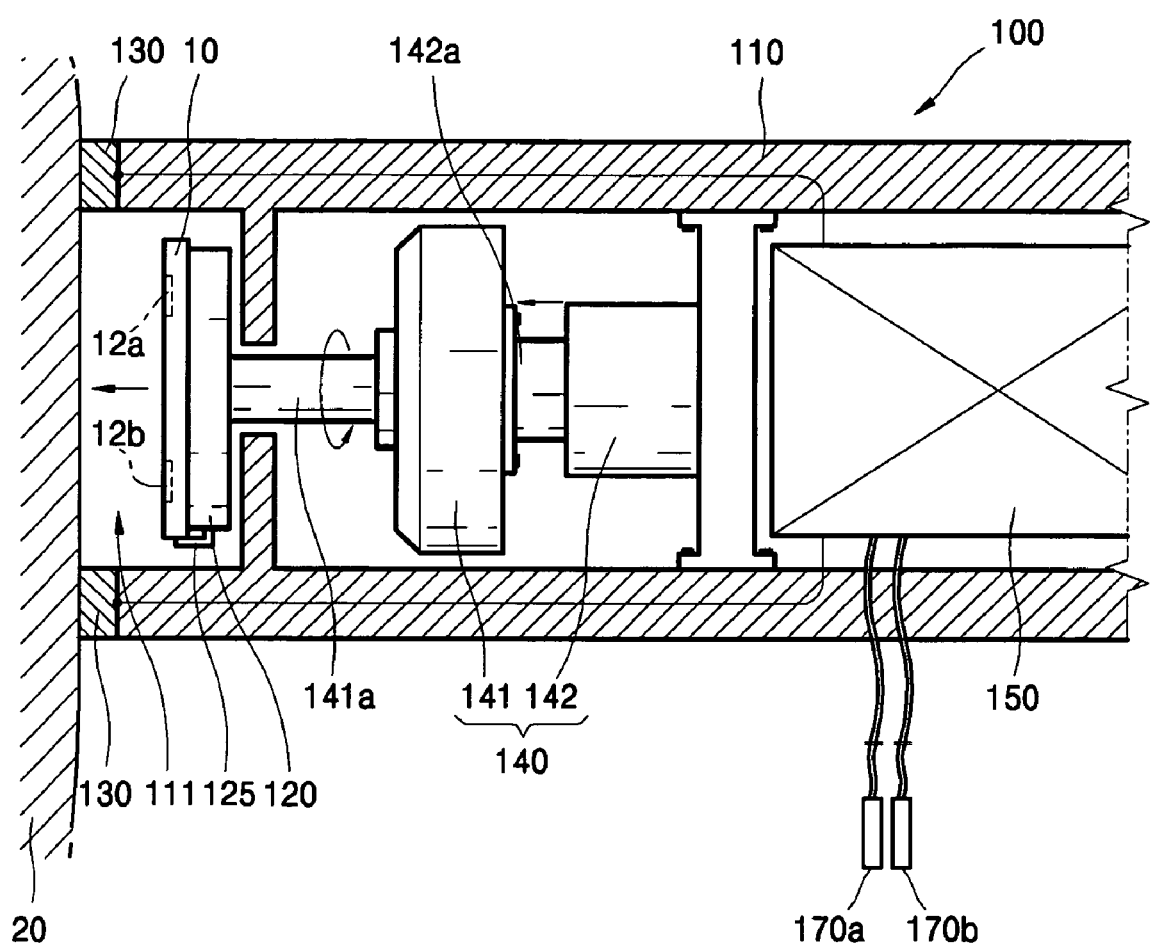
FIG. 2A is a partially cut-away sectional view showing the state before the biosignal measurement sensor is attached to a subject by the apparatus of FIG. 1A.
Figure 2B:
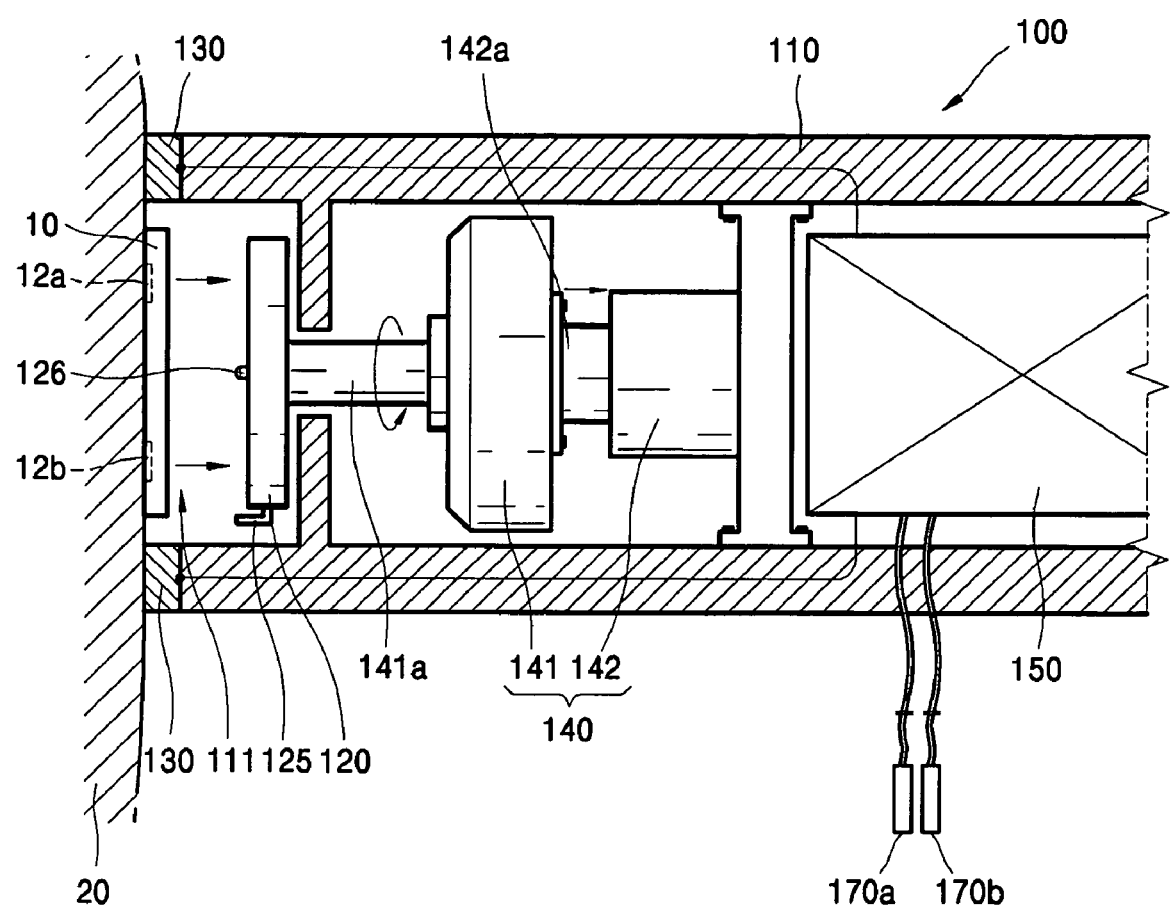
FIG. 2B is a partially cut-away sectional view showing the state after the biosignal measurement sensor is attached to a subject by the apparatus of FIG. 1A.

FIG. 1A is a perspective view of an apparatus for attaching a biosignal measurement sensor to a subject according to a non-limiting embodiment of the present invention. FIG. 1B is a block diagram showing the structure of a receiver to wireless communication with the biosignal measurement sensor. FIG. 2A is a partially cut-away sectional view showing the state before the biosignal measurement sensor is attached to a subject by the apparatus of FIG. 1A. FIG. 2B is a partially cut-away sectional view showing the state after the biosignal measurement sensor is attached to a subject by the apparatus of FIG. 1A.

Referring to FIGS. 1A through 2B, an apparatus 100 for attaching a biosignal measurement sensor to a subject includes a housing 110 having an opening 111 at an end portion thereof, an installation portion 120 installed in the opening 111 of the housing 110 capable of rotating and linearly moving, a plurality of detection electrodes 130 installed at the end portion of the housing 110 where the opening 111 is formed, an actuator 140 rotating and linearly moving the installation portion 120, and a circuit portion 150 electrically connected to the detection electrodes 130 and driving the actuator 140.

The opening 111 of the housing 110 has an almost circular shape so that the detection electrodes 130 can be arranged along the circumferential edge of the opening 111. The installation portion 120 has a disc shape corresponding to the shape of the opening 111. Also, the installation portion 120 may have various shapes other than the disc shape as shown in the drawings as long as it can rotate in the opening 111.

A biosignal measurement sensor 10 is installed at the installation portion 120. The biosignal measurement sensor 10 includes a patch 11 in which an adhesive material is coated on a side thereof attached to a subject 20, and a pair of sensor electrodes 12a and 12b included in the patch 11. One of the sensor electrodes 12a and 12b is a positive electrode while the other one is a negative electrode. The biosignal measurement sensor 10 is used to measure electrocardiogram or electromyogram by being attached to the skin of the subject 20. The signals from the subject 20 measured by the sensor electrodes 12a and 12b can be transferred to a receiver 50 through RF unit 51 by wireless communication (see FIG. 1B).

The receiver 50 includes a sensor signal processing portion 53 for amplifying a difference between signals from the subject 20 measured by the sensor electrodes 12a and 12b, digitalizing the amplified signal difference, and generating sensor data, and a storing portion 55 for storing the sensor data generated by the sensor signal processing portion 53. The sensor data generated by the sensor signal processing portion 53 is stored in the storing portion 55 or displayed through a display portion 57. When the sensor signal processing portion 53 is located outside the patch 11, the sensor signal processing portion 53 may be connected to the sensor electrodes 12a and 12b by wire and receives the signals measured by the sensor electrodes 12a and 12b. The sensor signal processing portion 53 and the storing portion 55 may be included in the patch 11 with the sensor electrodes 12a and 12b to form the biosignal measurement sensor 10.

The installation portion 120 has a gripper 125 to grip and release the biosignal measurement sensor 10. The gripper 125, as shown in FIG. 2a, grips the biosignal measurement sensor 10 when the biosignal measurement sensor 10 is located at the installation portion 120 and fixed thereto. When the biosignal measurement sensor 10 is separated from the installation portion 120 to be attached to the subject 20, the gripper 125 releases the biosignal measurement sensor 10, as shown in FIG. 2B. The gripper 125 is controlled by the circuit portion 150. The gripper 125 is installed at the installation portion 120 capable of gripping the side portion of the biosignal measurement sensor 10. At least two grippers 125 are provided so that the biosignal measurement sensor 10 is stably gripped.

The installation portion 120 may include a position detection portion 126 to detect whether the biosignal measurement sensor 10 is located therein. Also, the position detection portion 126 is used to control the gripper 125. The position detection portion 126 transfers information to the circuit portion 150 to control the gripper 125. When the position detection portion 126 detects that the biosignal measurement sensor 10 is located at the installation portion 120, the circuit portion 150 receives the information and controls the gripper 125 to change from a release position to a grip position. When the position detection portion 126 detects that the biosignal measurement sensor 10 is not located at the installation portion 120, the circuit portion 150 receives the information and controls the gripper 125 to wait at a release position.

The information provided from the position detection portion 126 can be transferred to the circuit portion 150 and used to control the actuator 140. For example, when the position detection portion 126 detects that the biosignal measurement sensor 10 is not located at the installation portion 120, the circuit portion 150 receives the information and operates the actuator 140 such that the installation portion 120 waits at an entrance of the opening 111 of the housing 110 or waits in a state of protruding from the entrance. When the installation portion 120 waits at the entrance of the opening 111 of the housing 110, the biosignal measurement sensor 10 can be easily installed at the installation portion 120. When the position detection portion 126 detects that the biosignal measurement sensor 10 is located at the installation portion 120, the circuit portion 150 receives the information and operates the actuator 140 such that, when the biosignal measurement sensor 10 is fixed to the installation portion 120 by the gripper 125, the installation portion 120 moves inwardly from the entrance of the opening 111 of the housing 110 and waits there. When the installation portion 120 is moved inwardly from the entrance of the opening 111 of the housing 110, the biosignal measurement sensor 10 can rotate in a state of being separated from the subject 20 while the detection electrodes 130 contact the subject 20.

An identification mark 160 is provided at the installation portion 120 and the biosignal measurement sensor 10 so that the sensor electrodes 12a and 12b of the biosignal measurement sensor 10 can be arranged at designated positions on the installation portion 120. The identification mark 160, as shown in FIG. 1A, includes a groove 160a formed in the biosignal measurement sensor 10 and a protrusion 160b formed on the installation portion 120 to be inserted in the groove 160a. However, the identification mark 160 can be constructed in a variety of manners.

The actuator 140 for rotating and linearly moving the installation portion 120, as shown in FIGS. 2A and 2B, is configured with a combination of an actuator 141 for rotational movement and an actuator 142 for linear movement. The actuator 141 for rotational movement has a rotational movement portion 141a that is coupled to the center of the installation portion 120 so that the installation portion 120 can be rotated. The actuator 142 for linear movement has a linear movement portion 142a coupled to the actuator 141 for rotational movement so that the installation portion 120 can be linearly moved. A rotary step motor can be used as the actuator 141 for rotational movement while a linear step motor can be used as the actuator 142 for linear movement. A power button 181 and an operation button 182 are positioned at the outer surface of the housing 110.

The detection electrodes 130 are arranged at the side of the opening 111 of the housing 110 where the installation portion 120 is installed. The detection electrodes 130 are installed at the circumferential edge of the opening 111 of the housing 110 to contact the subject 20 and obtain voltage signals. The detection electrodes 130 are arranged around the installation portion 120 such that two opposite detection electrodes, with respect to the center of the arrangement, form a pair. The detection electrodes 130 are provided in an even number, such that pairs of detection electrodes are provided. Among each pair of the detection electrodes, one functions as a positive electrode while the other functions as a negative electrode. Thus, a voltage signal is obtained from the subject 20 like the sensor electrodes 12a and 12b of the biosignal measurement sensor 10. The detection electrodes 130 are provided in multiple pairs because it is necessary to obtain a voltage signal in various directions with respect to the subject 20.

Figure 3:
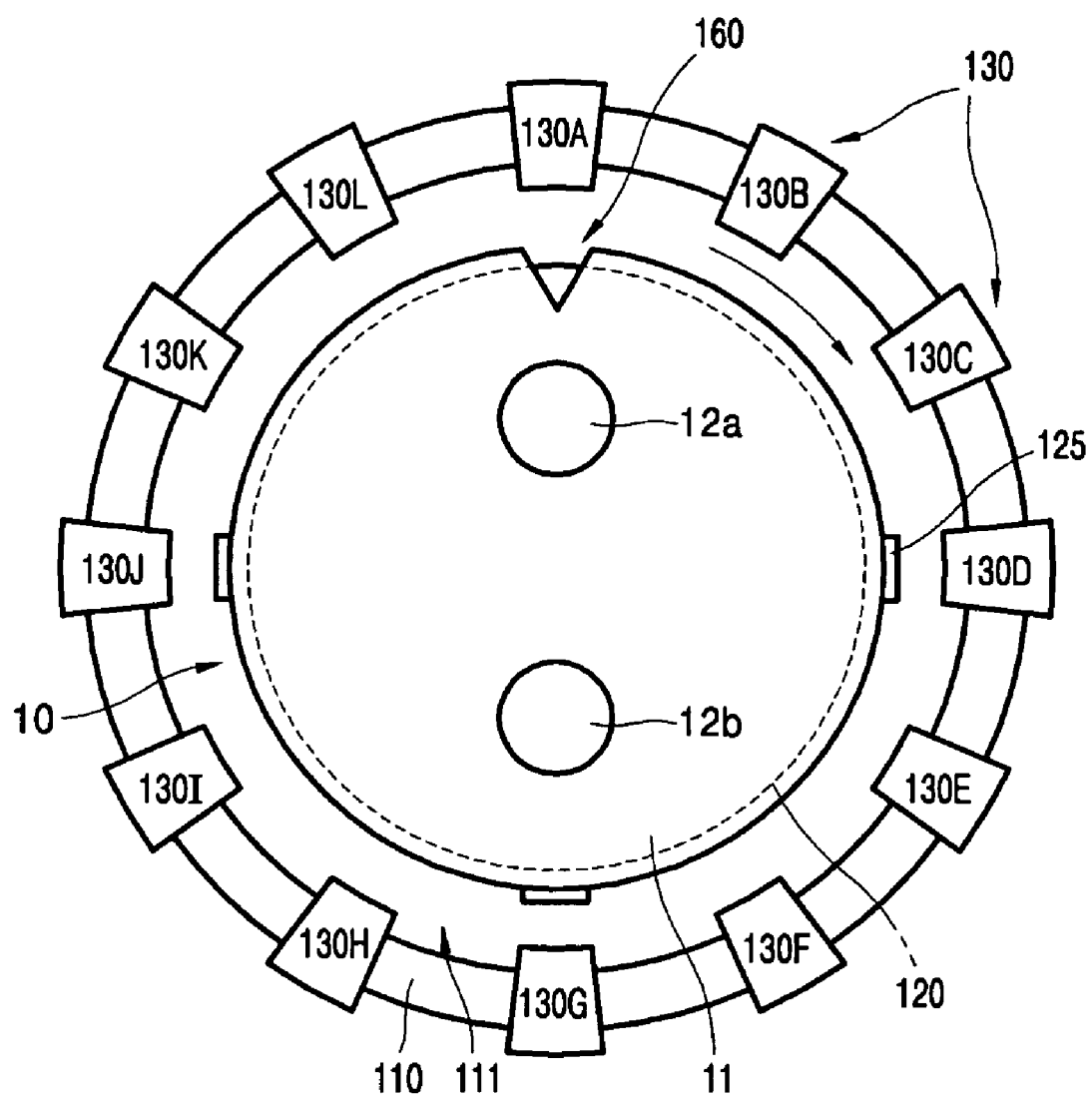
FIG. 3 is a front view showing the state in which the detection electrodes of the apparatus of FIG. 1A are arranged.

For example, as shown in FIG. 3, the twelve detection electrodes 130 which are first through twelve detection electrodes 130A, 130B, 130C, 130D, 130E, 130F, 130G, 130H, 130I, 130J, 130K, and 130L are circularly arranged at an interval of 30°. When the detection electrodes 130 are arranged in this way, voltage signals can be obtained from the twelve directions with respect to the subject 120. That is, in a pair of the first detection electrode 130A and the seventh detection electrode 130G, the first detection electrode 130A functions as a positive electrode while the seventh detection electrode 130G functions as a negative electrode, or the first detection electrode 130A functions as a negative electrode while the seventh detection electrode 130G functions as a positive electrode. In these cases, since the sensor electrodes 12a and 12b are arranged in different directions, voltage signals are obtained from two different directions. This is the same for a pair of the second detection electrode 130B and the eight detection electrode 130H, a pair of the third detection electrode 130C and the ninth detection electrode 130I, a pair of the fourth detection electrode 130D and the tenth detection electrode 130J, a pair of the fifth detection electrode 130E and the eleventh detection electrode 130K, and a pair of the sixth detection electrode 130F and the twelfth detection electrode 130L. Thus, when the twelve detection electrodes 130 are provided, the voltage signals can be obtained from twelve directions with respect to the subject 20.

As the detection electrodes 130 are configured as above, the voltage signals sequentially obtained from various directions with respect to the subject 20, that is, the twelve directions, are provided to the circuit portion 150 before the sensor electrodes 12a and 12b are attached to the subject 20. Thus, a direction in which an optimal voltage signal of the provided voltage signals is obtained, can be searched so that the sensor electrodes 12a and 12b are arranged and attached in the same searched direction. Thus, not only an expert, but also a novice, can attach the biosignal measurement sensor 10 to the subject 20 with the sensor electrodes 12a and 12b arranged accurately and easily. As a result, an accurate biosignal is obtained so that accurate diagnosis can be made. Also, in the electrocardiogram test, accurate diagnosis can be made even when the position of the heart of a patient varies. The sensor electrodes 12a and 12b can be arranged at positions where more accurate voltage signals are obtained as the number of voltage signals obtained by the detection electrodes 130 increases. Although the twelve detection electrodes are provided in this embodiment, the number of the detection electrodes in the present invention is not limited thereto.

The detection electrodes 130 are electrically connected to the circuit portion 150 such that the voltage signals obtained by the detection electrodes 130 are provided to the circuit portion 150 to be processed. The circuit portion 150 processes the voltage signals obtained by each pair of the detection electrodes 130 and generates detection data. Then, the circuit portion 150 searches for a pair of the detection electrodes 130 that provides the optimal detection data and generates a control signal for driving the actuator 140 based on the searched result. The control signal is transmitted to the actuator 140 and the actuator 140 rotates the installation portion 120 so that the sensor electrodes 12a and 12b are arranged in the same direction as the pair of detection electrodes 130 that provides the optimal detection data, and moves the installation portion 120 to the subject 20 so that the sensor electrodes 12a and 12b are attached to the subject 20. The optimal detection data may correspond to the detection data having the maximum correlation coefficient by comparing the detection data with reference data or the detection data having the maximum peak among the detection data.

Figure 4:
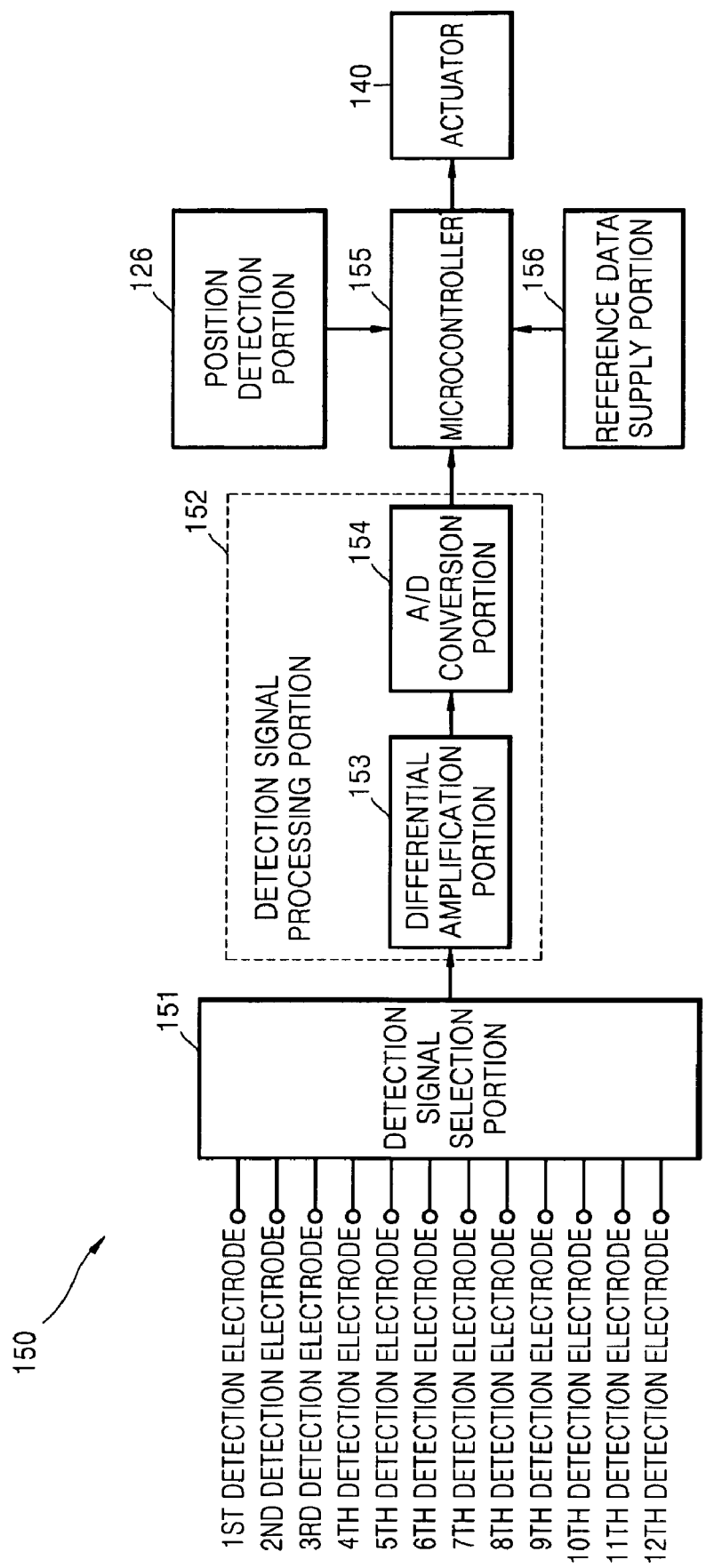
FIG. 4 is a block diagram of an example of the circuit portion driving the apparatus of FIG. 1A.

FIG. 4 is a block diagram of an example of the circuit portion 150 driving the apparatus of FIG. 1A. Referring to FIG. 4, the circuit portion 150 includes a detection signal selection portion 151 for sequentially selecting two detection signals received from each pair of the detection electrodes 130, a detection signal processing portion 152 for processing the detection signals that are sequentially received from the detection signal selection portion 151 and generating detection data, and a microcontroller 155 for comparing the detection data generated by the detection signal processing portion 152 with reference data provided by a reference data supply portion 156 and generating a control signal to drive the actuator 140 based on the result of comparison. The circuit portion 150 further includes a power supply portion. Power can be supplied or cut off with respect to the circuit portion 150 using the power button 181 of FIG. 1A. The microcontroller 155 can be controlled by the operation button 182 of FIG. 1A.

When the detection electrodes 130 are configured as shown in FIG. 3, the detection signal selection portion 151 selects the detections signals output from a pair of the first and seventh detection electrodes 130A and 130G, the detections signals output from a pair of the second and eighth detection electrodes 130B and 130H, the detections signals output from a pair of the third and ninth detection electrodes 130C and 130I, the detections signals output from a pair of the fourth and tenth detection electrodes 130D and 130J, the detections signals output from a pair of the fifth and eleventh detection electrodes 130E and 130K, and the detections signals output from a pair of the sixth and twelfth detection electrodes 130F and 130L. Since the detection signals selected when the first detection electrode 130A is a positive electrode while the seventh electrode 130G is a negative electrode are different from those selected when the first detection electrode 130A is a negative electrode while the seventh electrode 130G is a positive electrode, the detection signal selection portion 151 separately selects the detection signals according to the type of electrode. The same goes for the pair of the second and eighth detection electrodes 130B and 130H, the third and ninth detection electrodes 130C and 130I, the pair of the fourth and tenth detection electrodes 130D and 130J, the pair of the fifth and eleventh detection electrodes 130E and 130K, and the pair of the sixth and twelfth detection electrodes 130F and 130L.

The two detection signals selected by the detection signal selection portion 151 are transferred to the detection signal processing portion 152 and processed therein to generate detection data. The detection signal processing portion 152 generates the detection data by amplifying and digitalizing the difference between the detection signals. For this purpose, the detection signal processing portion 152 further includes a differential amplification portion 153 for amplifying the difference between the detection signals and an A/D conversion portion 154 for converting an analog signal received from the differential amplification portion 153 into a digital signal. The detection signal processing portion 152 further includes a filtering portion (not shown).

The detection data generated by the detection signal processing portion 152 is transferred to the microcontroller 155. The microcontroller 155 calculates a correlation coefficient by comparing the received detection data with the reference data provided by the reference data supply portion 156, searches for the detection electrode 130 having the maximum correlation coefficient, and generates a control signal to drive the actuator 140 based on the searched result. The control signal is transferred to the actuator 140. The actuator 140 rotates the installation portion 120 such that the sensor electrodes 12a and 12b can be arranged identical with the direction in which the detection electrodes 130 providing the detection data having the maximum correlation coefficient are arranged. Then, the actuator 140 moves the installation portion 120 toward the subject 20 so that the sensor electrodes 12a and 12b are attached to the subject 20. In the meantime, the microcontroller 155 can search for the detection data having the maximum peak among the detection data provided by the detection electrodes 130 and generate the control signal to drive the actuator based on the search result as described above. In this case, the reference data supply portion 156 can be omitted. The microcontroller 155 receives information from the position detection portion 126 for detecting whether the biosignal measurement sensor 10 is located at the installation portion 120 and generates the control signal to drive the actuator 140 and the gripper 125 as described above.

Figure 5:
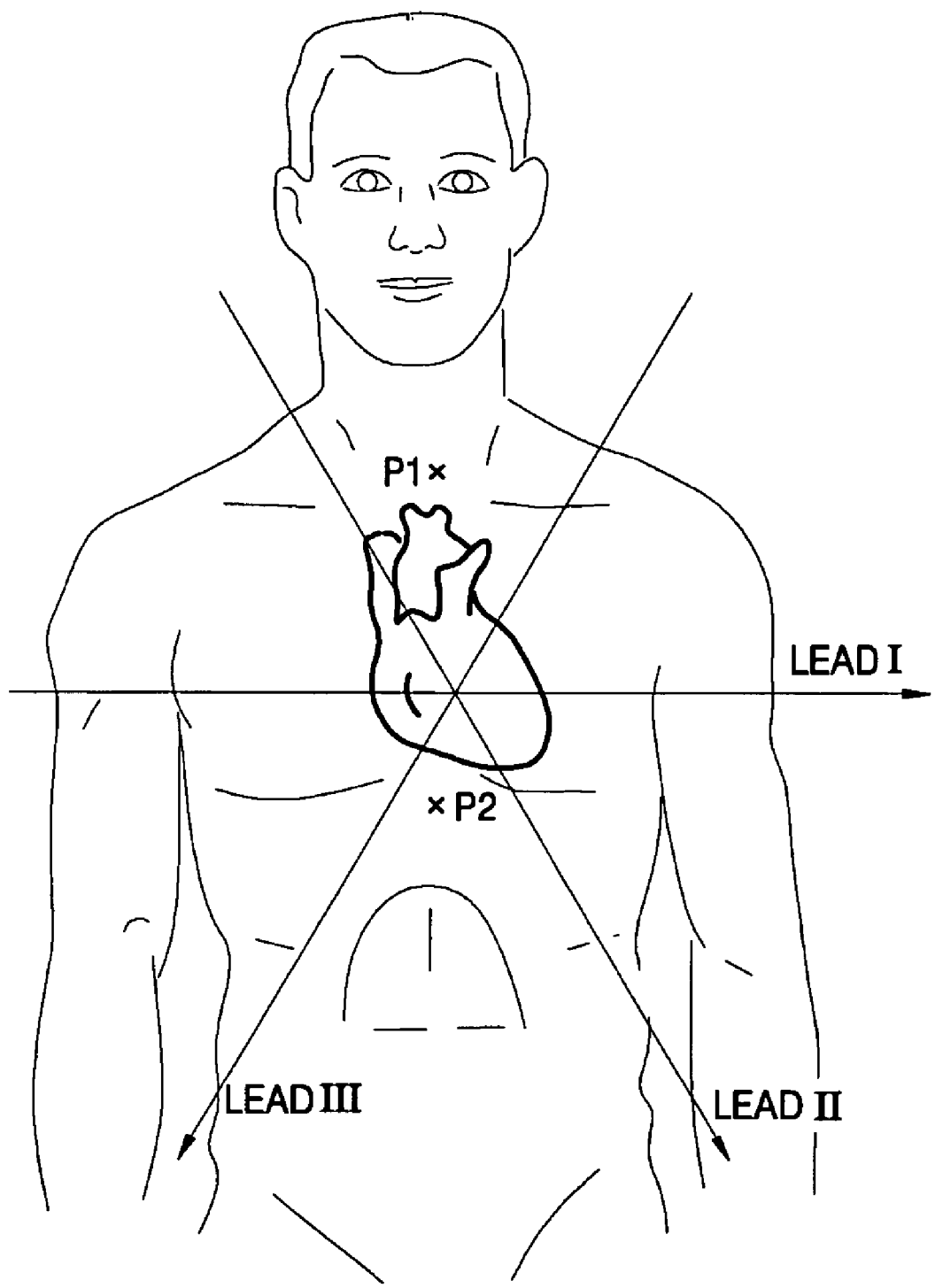
FIG. 5 is a view showing the lead I, lead II, and lead III in the electrocardiogram.

The reference data provided by the reference data supply portion 156 is obtained using a pair of reference electrodes 170a and 170b, as shown in FIG. 1A. The reference electrodes 170a and 170b are attached at reference positions on the subject 20 to obtain voltage signals from the subject 20. For the comparison with the detection data, the reference data obtained by the reference electrodes 170a and 170b is obtained by amplifying a difference between the signals of the reference electrodes 170a and 170b and digitalizing the amplified difference. When an electrocardiogram is measured, the reference positions where the reference electrodes 170a and 170b are attached can be set to positions where signals can be obtained in one of standard limb lead methods including lead I, lead II, and lead III shown in FIG. 5. However, the present invention is not limited to the above method. The reference electrodes 170a and 170b can be omitted.

Alternatively, the reference data is set to typical electrocardiogram data obtained in one of the standard limb lead methods including the lead I, lead Ii, and lead III and stored in the reference data supply portion 156. The stored data is provided to the microcontroller 155.

Figure 6:
FIG. 6 is a pattern diagram showing an example of an electrocardiogram signal led by the lead II of FIG. 5.
Figure 7A:
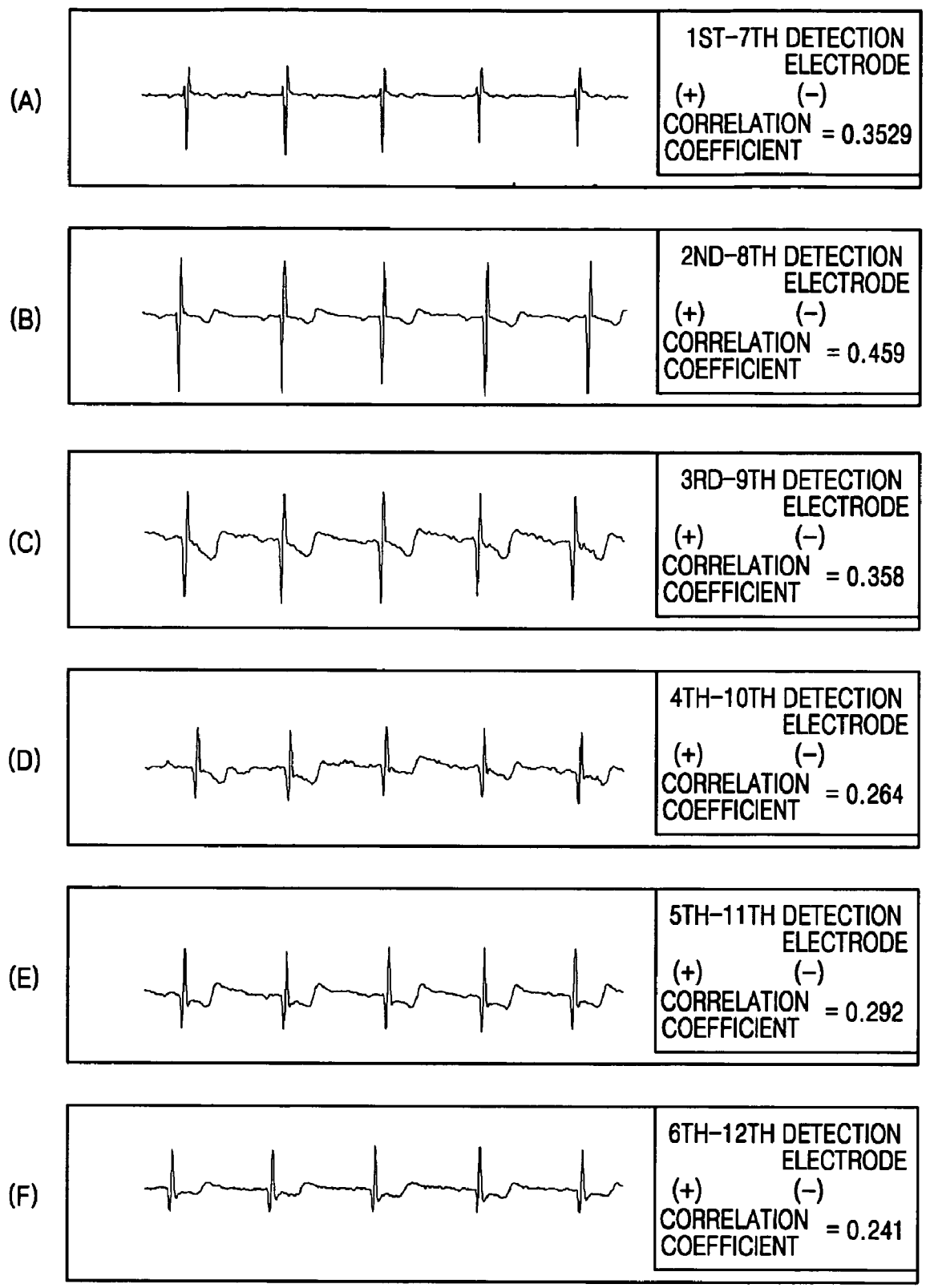
FIGS. 7A and 7B are pattern diagrams showing the twelve electrocardiogram signals detected when the apparatus of FIG. 1A is located at the position P1 of FIG. 5.
Figure 7B:
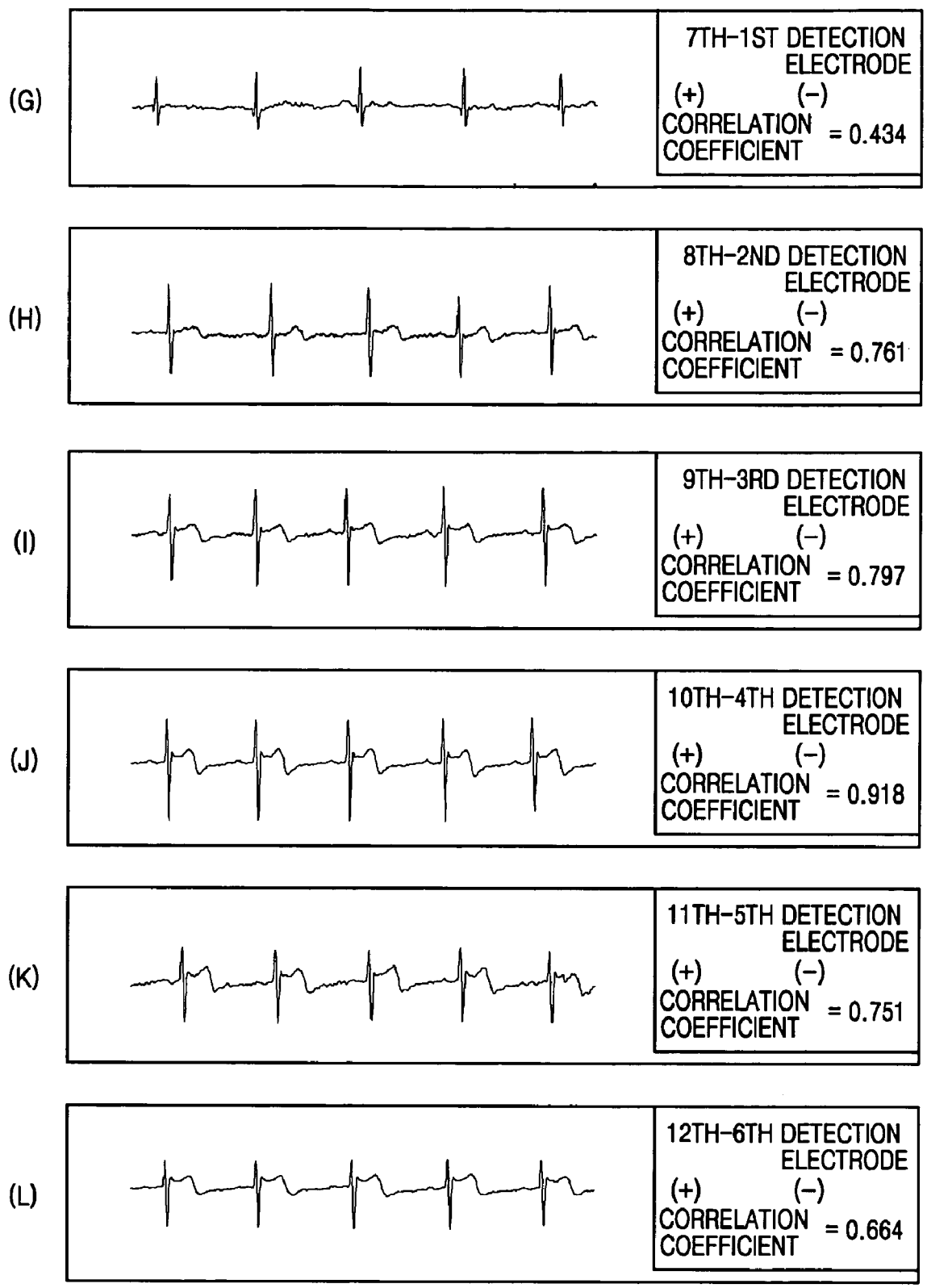
Figure 8A:
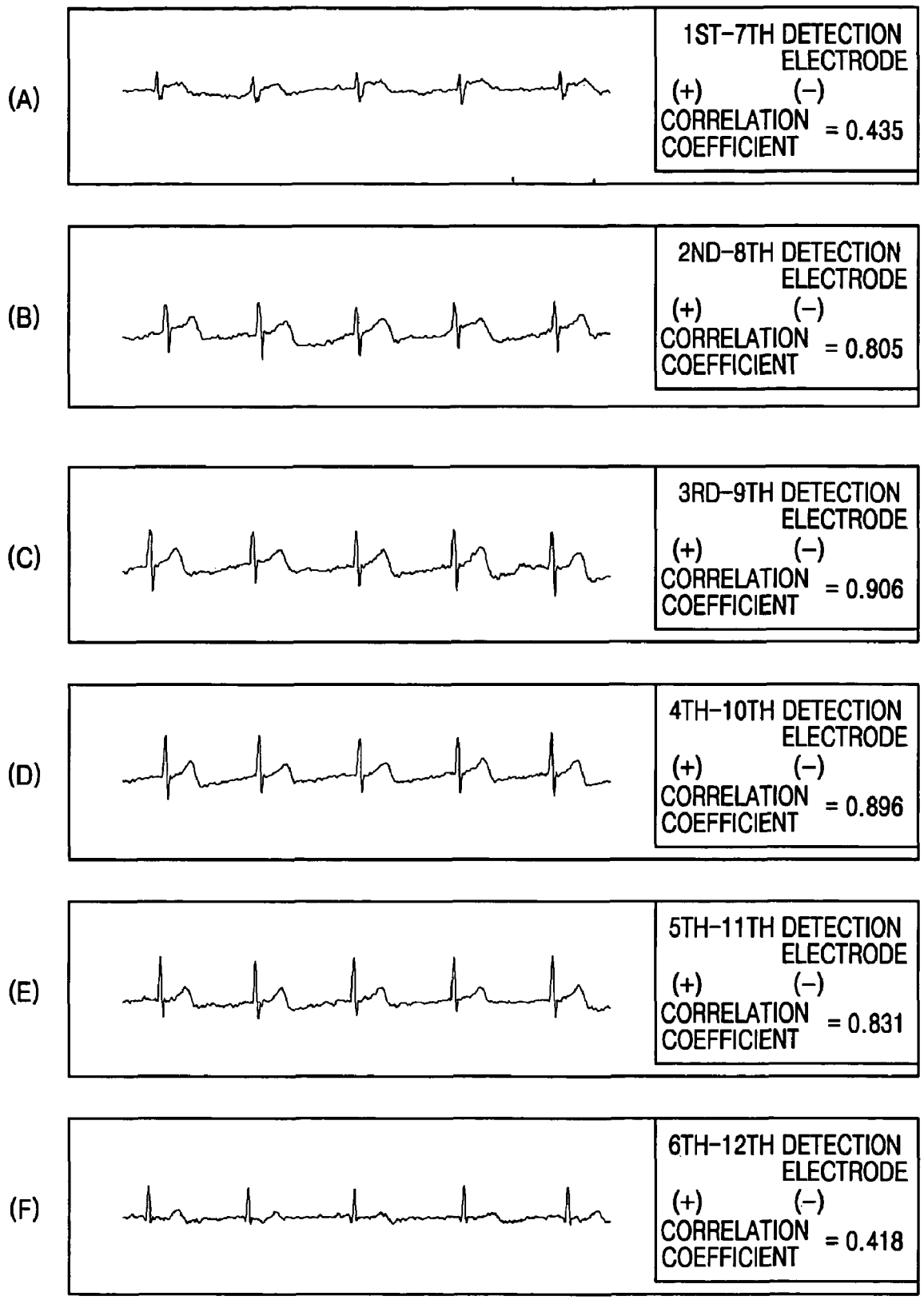
FIGS. 8A and 8B are pattern diagrams showing the twelve electrocardiogram signals detected when the apparatus of FIG. 1A is located at the position P2 of FIG. 5.
Figure 8B:
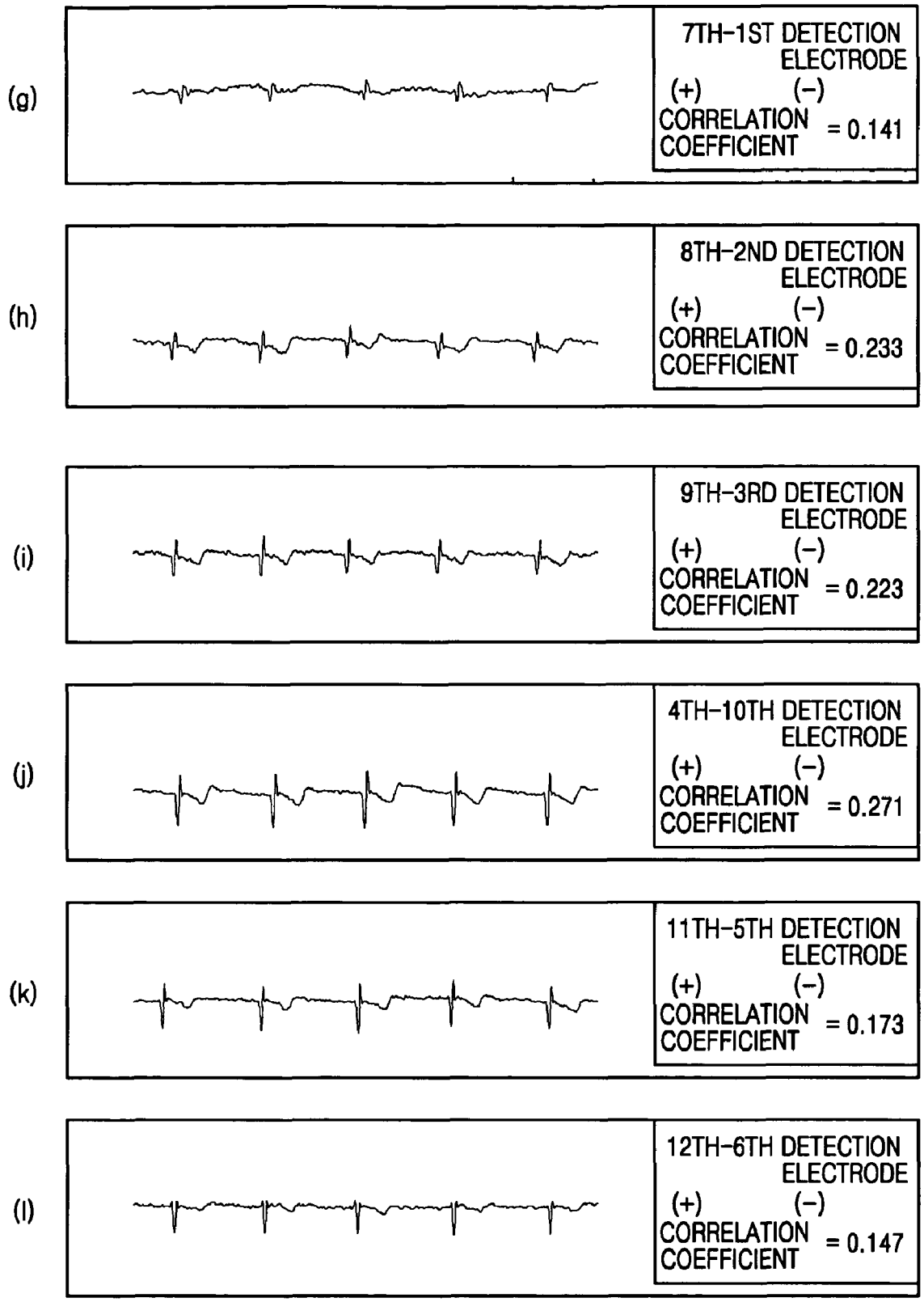

FIG. 6 shows an example of a typical electrocardiogram signal led by the lead II of the above standard limb lead method. An example of searching detection data having the maximum correlation coefficient using the electrocardiogram signal shown in FIG. 6 as the reference data is described below with reference to FIGS. 7A through 8B. FIGS. 7A and 7B show patterns of twelve electrocardiogram signals detected when the apparatus of FIG. 1A is located at a position P1 of FIG. 5. FIGS. 8A and 8B show patterns of twelve electrocardiogram signals detected when the apparatus of FIG. 1A is located at a position P2 of FIG. 5. The apparatus of FIG. 1A contacts the subject with the first detection electrode located at the uppermost position and the seventh detection electrode located at the lowermost position.

In FIGS. 7A and 7B, when a correlation coefficient is calculated by comparing the twelve electrocardiogram signals detected from each of the pairs made by the first through twelve detection electrodes with the electrocardiogram signal of FIG. 6, it can be seen that the electrocardiogram signal shown in pattern (j) has the maximum correlation coefficient among the twelve electrocardiogram signals shown in patterns (a) through (l). The electrocardiogram signal shown in the pattern (j) is detected from a pair of the tenth detection electrode that is a positive electrode and the fourth detection electrode that is a negative electrode.

In FIGS. 8A and 8B, when a correlation coefficient is calculated by comparing the twelve electrocardiogram signals detected from each of the pairs made by the first through twelve detection electrodes with the electrocardiogram signal of FIG. 6, it can be seen that the electrocardiogram signal shown in pattern (c) has the maximum correlation coefficient among the twelve electrocardiogram signals shown in patterns (a) through (l). The electrocardiogram signal shown in the pattern (c) is detected from a pair of the fourth detection electrode that is a positive electrode and the tenth detection electrode that is a negative electrode.

The apparatus for attaching a biosignal measurement sensor configured as above to a subject can attach the biosignal measurement sensor to the subject in the method shown in FIG. 9.

A biosignal measurement sensor having a pair of sensor electrodes is arranged at an installation portion located at an entrance of an opening of a housing (210). In the installation portion, a position detection portion detects the location of the biosignal measurement sensor so that a gripper is operated to grip the biosignal measurement sensor and installed the same. After the biosignal measurement sensor is installed, the installation portion moves back from the entrance of the opening of the housing and waits therein.

Then, the detection electrode pairs arranged along the circumference to face each other, are made to contact the subject as a whole to provide detection signals from the detection electrodes to a circuit portion (220). When a pair of reference electrodes are further provided, the reference electrodes are attached at reference positions on the subject so that reference signals can be provided from the reference electrodes to the circuit portion.

The circuit portion which received the detection signals and the reference signals, is operated to process the voltage signals obtained from the detection electrode pairs and generate detection data (230).

Then, the circuit portion searches for a pair of detection electrodes that provided an optimal detection data of the detection data (240). A control signal to drive an actuator is generated based on the search result and transferred to the actuator. The searched optimal detection data corresponds to detection data having the maximum correlation coefficient or detection data having the maximum peak of the detection data, which is obtained by comparing the detection data with either reference data provided by the reference electrodes or previously stored reference data.

Next, the installation portion is rotated by the actuator that received a control signal from the circuit portion such that sensor electrodes are arranged in the same direction in which the detection electrodes that provided the optimal detection data are arranged (250).

Finally, the actuator moves the installation portion toward the subject so that the biosignal measurement sensor is attached to the subject (260). After the biosignal measurement sensor is attached to the subject, the gripper is operated to release the biosignal measurement sensor. Then, the installation portion is moved into the housing so that the biosignal measurement sensor is separated from the installation portion. Accordingly, since the overall apparatus is completely separated from the subject once the biosignal measurement sensor is attached to the subject, the biosignal measurement sensor attached to the subject can measure a biosignal.

As described above, according to the present invention, not only an expert but also a novice can accurately and easily attach the biosignal measurement sensor at any position on the subject. Thus, the user's convenience is improved and also an accurate biosignal can be obtained so that accurate diagnosis can be obtained. Furthermore, in an electrocardiogram test, since the application of the apparatus is possible even when the position of the heart varies according to patients, accurate diagnosis can be obtained.

While this invention has been particularly shown and described with reference to non-limiting embodiments thereof, it will be understood by those skilled in the art that various changes in form and details may be made therein without departing from the spirit and scope of the invention as defined by the appended claims.

What is claimed is:

1. An apparatus for attaching a biosignal measurement sensor to a subject, the apparatus comprising:
    a housing having an open space at one side;
    an installation portion rotatably installed in the open space, on which the biosignal measurement sensor is installed, the biological measurement sensor having a pair of sensor electrodes;
    a plurality of detection electrodes on the one side of the housing so as to be arranged along a circumferential edge of the installation portion, and forming pairs of detection electrodes that face each other with respect to a center of arrangement along the circumferential edge;
    an actuator installed in the housing, the actuator operative to rotate and linearly move the installation portion; and
    a circuit portion that searches for detection electrodes that provide optimal detection data based on a difference in signals between each pair of detection electrodes, and drives the actuator to allow the pair of sensor electrodes provided at the biosignal measurement sensor to be arranged in a same direction in which the searched detection electrodes are arranged,
    wherein the detection electrodes comprise at least twelve detection electrodes arranged along the circumferential edge of the installation portion at a constant interval.

2. The apparatus as claimed in claim 1, wherein the optimal detection data is detection data having a maximum correlation coefficient with respect to reference data.

3. The apparatus as claimed in claim 2, wherein the circuit portion comprises a microcontroller operative to search the detection electrodes having the detection data having the maximum correlation coefficient by calculating correlation coefficients between the detection data and the reference data, and the microcontroller is operative to provide a control signal to the actuator to arrange the sensor electrodes in the same direction in which the searched detection electrodes are arranged.

4. The apparatus as claimed in claim 3, wherein the circuit portion comprises:
    a detection signal selection portion operative to sequentially select two detection signals output from each pair of the detection electrodes; and
    a detection signal processing portion operative to amplify a difference between the detection signals received from the detection signal selection portion and the detection signal processing portion is operative to digitalize the amplified signal difference to generate detection data and provide the generated detection data to the microcontroller.

5. The apparatus as claimed in claim 4, wherein the detection signal processing portion comprises:
    a differential amplification portion operative to amplify the signal difference between the detection signals received from the detection signal selection portion; and
    an A/D conversion portion operative to correct an analog signal received from the differential amplification portion into a digital signal.

6. The apparatus as claimed in claim 2, wherein the reference data is data obtained by amplifying a difference between signals of reference electrodes attached at a reference position of the subject and digitalizing the amplified signal difference.

7. The apparatus as claimed in claim 6, wherein the reference position where the reference electrodes are attached is a position where a signal is obtained in one of a standard limb lead method including a lead I, a lead II, and a lead III, when an electrocardiogram is measured.

8. The apparatus as claimed in claim 2, wherein the reference data is data obtained in one of a standard limb lead methods including a lead I, a lead II, and a lead III, when an electrocardiogram is measured.

9. The apparatus as claimed in claim 1, wherein the optimal detection data is detection data having a maximum peak.

10. The apparatus as claimed in claim 9, wherein the circuit portion comprises a microcontroller operative to search detection electrodes having detection data with a maximum correlation coefficient by calculating correlation coefficients between detection data and reference data, and providing a control signal to the actuator to allow the sensor electrodes to be arranged in the same direction in which the searched detection electrodes are arranged.

11. The apparatus as claimed in claim 10, wherein the circuit portion comprises:
    a detection signal selection portion operative to sequentially select two detection signals output from each pair of the detection electrodes; and
    a detection signal processing portion operative to amplify a difference between the detection signals received from the detection signal selection portion and the detection signal processing portion operative to digitize the amplified signal difference to generate detection data and provide the generated detection data to the microcontroller.

12. The apparatus as claimed in claim 11, wherein the detection signal processing portion comprises:
   a differential amplification portion operative to amplify the signal difference between the detection signals received from the detection signal selection portion; and
   an A/D conversion portion operative to convert an analog signal received from the differential amplification portion into a digital signal.

13. The apparatus as claimed in claim 1, wherein a gripper capable of repeatedly performing gripping and releasing of the biosignal measurement sensor is provided at the installation portion.

14. The apparatus as claimed in claim 1, wherein a position detection portion operative to detect the biosignal measurement sensor is provided at the installation portion.

15. The apparatus as claimed in claim 14, wherein information provided by the position detection portion is transferred to the circuit portion and used to drive the gripper and the actuator.

16. The apparatus as claimed in claim 1, wherein a mark portion to facilitate arrangement of the sensor electrodes of the biosignal measurement sensor at a designated position on the installation portion is provided between the installation portion and the biosignal measurement sensor.

17. The apparatus as claimed in claim 1, wherein the actuator comprises an actuator for rotational movement which is coupled to the installation portion and rotates the installation portion, and an actuator for linear movement which is coupled to the actuator for rotational movement and linearly moves the installation portion.

18. The apparatus as claimed in claim 17, wherein the actuator for rotational movement is a rotary step motor and the actuator for linear movement is a linear step motor.

19. The apparatus as claimed in claim 1, wherein the biosignal measurement sensor is connected to the sensor signal processing portion by wire or in a wireless manner and the sensor signals measured by the sensor electrodes are transferred to the sensor signal processing portion and processed and stored therein.

20. The apparatus as claimed in claim 1, wherein the biosignal measurement sensor comprises:
   a sensor signal processing portion operative to amplify a difference between sensor signals measured from the sensor electrodes and operative to digitize the amplified signal difference to generate sensor data; and
   a storing portion operative to store the sensor data generated by the sensor signal processing portion.

21. A method of attaching the biosignal measurement sensor of claim 1, the method comprising:
   installing the biosignal measurement sensor on the installation portion;
   allowing the plurality of detection electrodes to contact a subject;
   obtaining detection data from a difference between signals of the detection electrodes forming each of the detection electrode pairs;
   searching detection electrodes having optimal detection data among the detection data;
   locating the biosignal measurement sensor by rotating the installation portion such that the sensor electrodes are arranged in the same direction in which the detection electrodes having the optimal detection data are arranged; and
   attaching the biosignal measurement sensor to the subject and then separating the installation portion from the biosignal measurement sensor.

22. The method as claimed in claim 21, wherein, in the searching of the detection electrodes, reference data is provided and detection data having a maximum correlation coefficient with respect to the reference data is searched.

23. The method as claimed in claim 22, wherein, in the allowing of the plurality of detection electrodes to contact a subject, a pair of reference electrodes are further provided, and further comprising attaching the reference electrodes at a reference position.

24. The method as claimed in claim 23, wherein the reference position where the reference electrodes are attached is a position where a signal is obtained in one of a standard limb lead methods including a lead I, a lead II, and a lead III, when an electrocardiogram is measured.

25. The method as claimed in claim 22, wherein the reference data is data obtained in one of a standard limb lead methods including a lead I, a lead II, and a lead III when an electrocardiogram is measured.

26. The method as claimed in claim 21, wherein, in the searching of the detection electrodes, detection data having a maximum peak is searched from the detection data.

* * * * *